(12) United States Patent
Hee-Hanson et al.

(10) Patent No.: US 12,274,873 B1
(45) Date of Patent: Apr. 15, 2025

(54) MEDICAMENT DELIVERY DEVICE

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/594,556

(22) Filed: Mar. 4, 2024

(51) Int. Cl.
  *A61M 5/32* (2006.01)
  *A61M 5/20* (2006.01)

(52) U.S. Cl.
  CPC ........ *A61M 5/3234* (2013.01); *A61M 5/3245* (2013.01); *A61M 5/2033* (2013.01); *A61M 2005/208* (2013.01)

(58) Field of Classification Search
  CPC . A61M 5/2033; A61M 5/20; A61M 2005/208
  See application file for complete search history.

(56) References Cited

U.S. PATENT DOCUMENTS

| | | | |
|---|---|---|---|
| 5,356,387 A | 10/1994 | Sirbola | |
| 7,597,685 B2 | 10/2009 | Olson | |
| 8,048,035 B2 | 11/2011 | Mesa et al. | |
| 8,945,063 B2 | 2/2015 | Wotton et al. | |
| 9,216,256 B2 | 12/2015 | Olson et al. | |
| 9,687,607 B2 * | 6/2017 | Brereton | A61M 5/326 |
| 10,569,019 B2 | 2/2020 | Hirschel et al. | |

(Continued)

FOREIGN PATENT DOCUMENTS

| | | |
|---|---|---|
| CH | 705345 A2 | 2/2013 |
| CH | 705992 A2 | 6/2013 |

(Continued)

OTHER PUBLICATIONS

Needle-based injection systems for medical use Requirements and test methods, Part 1: Needle injection systems, ISO 11608 1:2014(E), Third Edition, Switzerland, ISO, Dec. 15, 2014, pp. 1-13.

(Continued)

*Primary Examiner* — Laura A Bouchelle
(74) *Attorney, Agent, or Firm* — Fish & Richardson P.C.

(57) ABSTRACT

A medicament delivery device includes a needle disposed at a distal end of the medicament delivery device. The medicament delivery device includes a body for a syringe and a needle cover axially movable relative to the body between an extended position in which the needle cover covers the needle and a retracted position in which the needle protrudes from the distal end of the needle cover. The medicament delivery device includes a plunger axially movable relative to the body to dispense medicament from the medicament delivery device. The medicament delivery device includes a needle cover biasing mechanism configured to bias the needle cover distally from the retracted position to the extended position. The medicament delivery device includes a locking mechanism configured to be moved by the plunger from an initial configuration to an engaged configuration to prevent a distal movement of the needle cover biasing mechanism.

30 Claims, 10 Drawing Sheets

(56) References Cited

U.S. PATENT DOCUMENTS

| | | |
|---|---|---|
| 10,799,647 B2 | 10/2020 | Hostettler et al. |
| 11,116,911 B2 | 9/2021 | Wu |
| 11,383,044 B2 * | 7/2022 | Tschirren .......... A61M 5/31501 |
| 2004/0039336 A1 | 2/2004 | Amark et al. |
| 2005/0101919 A1 | 5/2005 | Brunnberg |
| 2007/0060840 A1 | 3/2007 | Conway |
| 2007/0112310 A1 | 5/2007 | Lavi et al. |
| 2007/0239117 A1 | 10/2007 | Chelak et al. |
| 2013/0289525 A1 | 10/2013 | Kemp et al. |
| 2017/0106146 A1 | 4/2017 | Folk et al. |
| 2019/0358400 A1 | 11/2019 | Nakamura et al. |
| 2020/0046909 A1 | 2/2020 | Hommann et al. |
| 2020/0289754 A1 | 9/2020 | Liscio et al. |
| 2021/0361881 A1 | 11/2021 | Garson et al. |
| 2021/0393886 A1 | 12/2021 | Nicolas et al. |

FOREIGN PATENT DOCUMENTS

| | | |
|---|---|---|
| EP | 3381490 B1 | 9/2020 |
| WO | WO 2002/047746 A1 | 6/2002 |
| WO | WO 2010/136077 A1 | 12/2010 |
| WO | WO 2018/011417 A1 | 1/2018 |
| WO | WO 2021/160540 A1 | 8/2021 |
| WO | WO 2021/197804 A1 | 10/2021 |
| WO | WO 2022/069617 A1 | 4/2022 |
| WO | WO 2022/184388 A1 | 9/2022 |
| WO | WO 2022/223789 A1 | 10/2022 |
| WO | WO 2023/057578 A1 | 4/2023 |

OTHER PUBLICATIONS

U.S. Appl. No. 18/594,683, filed Mar. 4, 2024, Alexander Hee-Hanson.

U.S. Appl. No. 18/594,643, filed Mar. 4, 2024, Alexander Hee-Hanson.

U.S. Appl. No. 18/594,597, filed Mar. 4, 2024, Alexander Hee-Hanson.

* cited by examiner

MEDICAMENT DELIVERY DEVICE

TECHNICAL FIELD

This application relates to a medicament delivery device for delivery of a medicament, for example an injector device such as an auto-injector device.

BACKGROUND

Injector devices are used to deliver a range of medicaments. In an auto-injector device, some or all of the actions required to use the injector device in administering medicament to a user are automated.

It is known to provide an auto-injector device having a needle cover which is axially movable to cover and uncover a needle, with the needle cover being biased by a spring to extend over the needle. Typically, the user presses the needle cover against an injection site, against the force of the spring, to push the needle cover into the housing and to uncover the needle which is pushed into the injection site. Medicament is automatically dispensed from the needle via an automated mechanism. A user typically holds the needle cover in a holding position for a predetermined period of time, to ensure that the correct dose of medicament is dispensed from the device, before removing the device from the injection site.

Some users find it difficult to fully depress the needle cover due to the force required or the change in force experienced during the activation movement. This may result in the needle not entering the user's skin to the correct depth, pain, discomfort, a wet injection site, early device removal and/or partial delivery of the medicament.

SUMMARY

A first aspect of this disclosure provides medicament delivery device comprising:
- a needle for injecting medicament into a user, the needle disposed at a distal end of the medicament delivery device;
- a body for containing a pre-filled syringe;
- a needle cover axially movable relative to the body between an extended position, in which the needle cover covers the needle, and a retracted position, in which the needle protrudes from the distal end of the needle cover;
- a plunger axially movable relative to the body from a proximal position to a distal position to dispense medicament from the medicament delivery device;
- a needle cover biasing mechanism configured to bias the needle cover distally from the retracted position to the extended position; and
- a locking mechanism configured to be moved by the plunger from an initial configuration to an engaged configuration to prevent a distal movement of the needle cover biasing mechanism.

Distal movement of the plunger from its proximal position may cause the locking mechanism to be moved from its initial configuration to its engaged configuration.

The needle cover biasing mechanism may prevent movement of the locking mechanism from its initial configuration until the needle cover has moved to its retracted position.

The needle cover biasing mechanism may comprise a shuttle member and a spring, wherein the spring is configured to exert a biasing force on the shuttle member which biases the shuttle member axially, towards the distal end of the medicament delivery device, and the shuttle member is configured to transfer the biasing force to the needle cover to bias the needle cover distally from the retracted position to the extended position.

The needle cover biasing mechanism may comprise one or more first slots and the locking mechanism may comprise one or more resilient members, wherein the one or more resilient members may each be configured to enter a respective one of the one or more first slots after movement of the locking mechanism from its initial configuration to its engaged configuration by the plunger, to prevent a distal movement of the needle cover biasing mechanism.

The one or more resilient members may each comprise a flexible arm and a first protrusion disposed on an end of the flexible arm, wherein each first protrusion of the one or more resilient members may be configured to enter a respective one of the one or more first slots after movement of the locking mechanism from its initial configuration to its engaged configuration by the plunger, to prevent a distal movement of the needle cover biasing mechanism.

The one or more resilient members may each be held in a respective one of the one or more first slots by an outer surface of the plunger while the plunger moves between its proximal position and distal position, to prevent a distal movement of the needle cover biasing mechanism.

The one or more resilient members may be configured to disengage from the respective one of the one or more first slots when the plunger is in its distal position.

The one or more first slots may be recesses or apertures.

The plunger may comprise one or more second slots, and the one or more resilient members may each be configured to engage a respective one of the one or more second slots when the locking mechanism is in its initial configuration, to inhibit distal movement of the plunger from its proximal position.

The one or more second slots may be recesses or apertures.

A distal-facing edge of each of the one or more second slots may be beveled or a proximal-facing edge of each of the one or more second protrusions may be beveled.

The one or more resilient members may each be configured to disengage the respective one of the one or more second slots responsive to the needle cover being moved to its retracted position.

The medicament delivery device may further comprise a drive spring configured to exert a driving force on the plunger which biases the plunger axially, towards the distal end of the medicament delivery device.

The medicament delivery device may further comprise the pre-filled syringe.

A second aspect of this disclosure provides a medicament delivery device comprising: a body for containing a pre-filled syringe;
- a needle cover axially movable relative to the body between an extended position, in which the needle cover covers a needle coupled to the pre-filled syringe, and a retracted position, in which the needle protrudes from the distal end of the needle cover;
- a plunger configured to dispense medicament from the medicament delivery device;
- a needle cover biasing mechanism configured to bias the needle cover from the retracted position to the extended position; and
- a locking mechanism configured to be actuated by a first movement of the plunger such that the locking mechanism inhibits the needle cover biasing mechanism from biasing the needle cover to the extended position.

The needle cover biasing mechanism may comprise a shuttle member and a biasing member, wherein the biasing member is configured to exert a biasing force on the shuttle member to bias the needle cover from the retracted position to the extended position.

The shuttle member and the needle cover may be integrally formed.

The biasing member may comprise a spring.

The locking mechanism may comprise a resilient member configured to be deflected by the first movement of the plunger to inhibit the needle cover biasing mechanism from biasing the needle cover to the extended position.

The resilient member may be configured to be deflected by the first movement of the plunger to engage a first slot provided at the needle cover biasing mechanism, to inhibit the needle cover biasing mechanism from biasing the needle cover to the extended position.

The resilient member may comprise a flexible arm and a first protrusion disposed on an end of the flexible arm, wherein the first protrusion is configured to enter the first slot to inhibit the needle cover biasing mechanism from biasing the needle cover to the extended position.

The resilient member may be configured to be held in engagement with the first slot by an outer surface of the plunger during a second movement of the plunger, the second movement subsequent to the first movement.

The second movement may occur during medicament delivery.

The resilient member may be configured to disengage from the first slot during a third movement of the plunger to cause the needle cover biasing mechanism to bias the needle cover to the extended position, the third movement subsequent to the second movement.

The third movement may correspond to a completion of medicament delivery.

The first movement, second movement and third movements may be axial movements.

The plunger may comprise a second slot, and the resilient member may be configured to engage the second slot while the needle cover is in its extended position to inhibit the first movement of the plunger.

The resilient member may be configured to disengage the second slot responsive to the needle cover being moved to its retracted position, to allow the first movement of the plunger.

The medicament delivery device may further comprise a drive spring configured to move the plunger.

The medicament delivery device may further comprise the pre-filled syringe.

BRIEF DESCRIPTION OF THE DRAWINGS

Exemplary embodiments are described with reference to the accompanying drawings, in which.

DETAILED DESCRIPTION

Figure 1A:
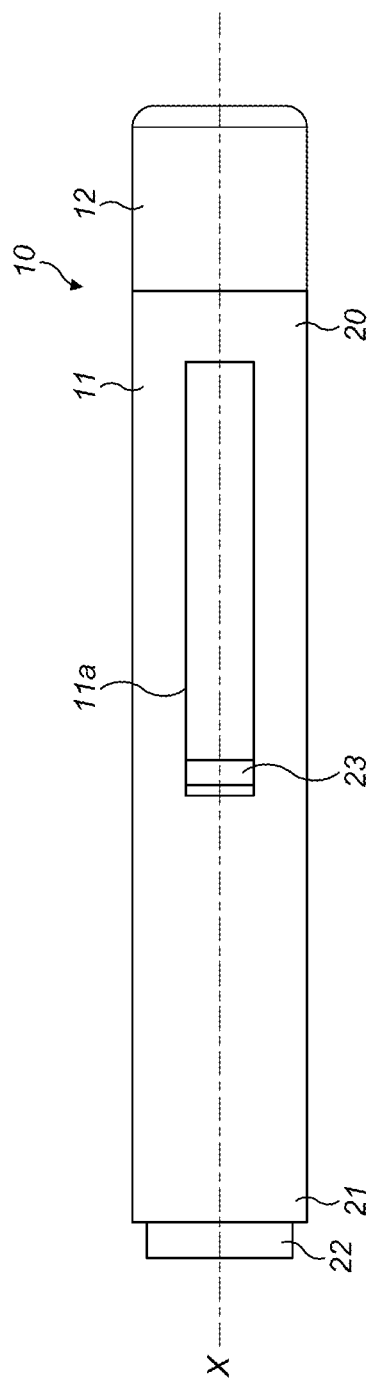
FIG. 1A shows an injector device with a cap attached.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
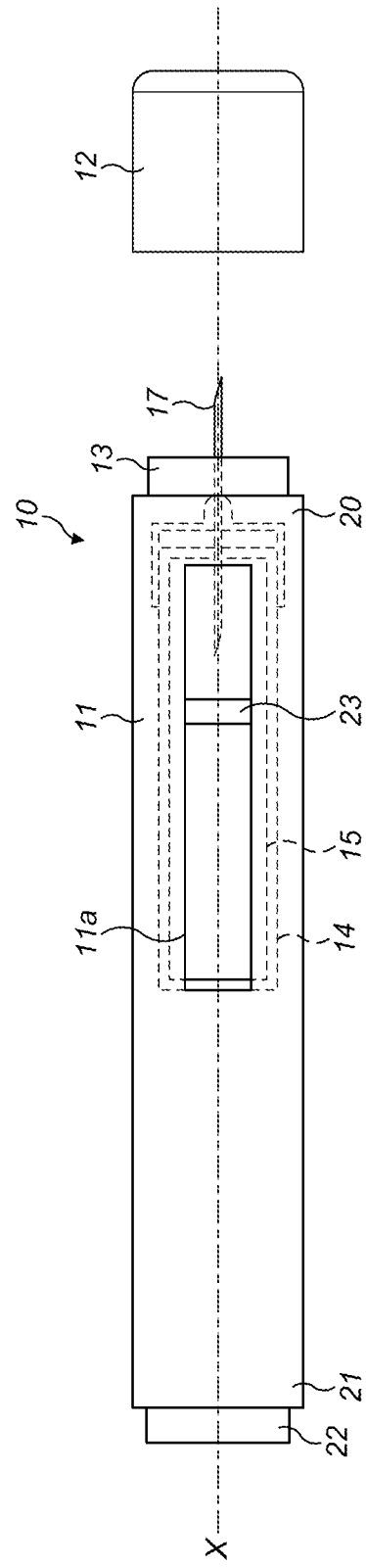
FIG. 1B shows the injector device of FIG. 1A with the cap removed.

According to some embodiments of the present disclosure, an exemplary drug delivery device 10 is shown in FIGS. 1A & 1B. Device 10, as described above, is configured to inject a medicament 15 into a patient's body. Device 10 includes a housing 11 which typically contains a reservoir 14 containing the medicament 15 to be injected (e.g., a syringe) and the components required to facilitate one or more steps of the delivery process. Device 10 can also include a cap assembly 12 that can be detachably mounted to the housing 11. Typically, a user removes cap 12 from housing 11 before device 10 can be operated. Device 10 can include a window 11a through which a user may view medicament 15 remaining in the reservoir 14.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe to a more distal location within the syringe in order to force a medicament 15 from the syringe through needle 17. In some embodiments, a drive spring is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament 15 within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring, located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2C:
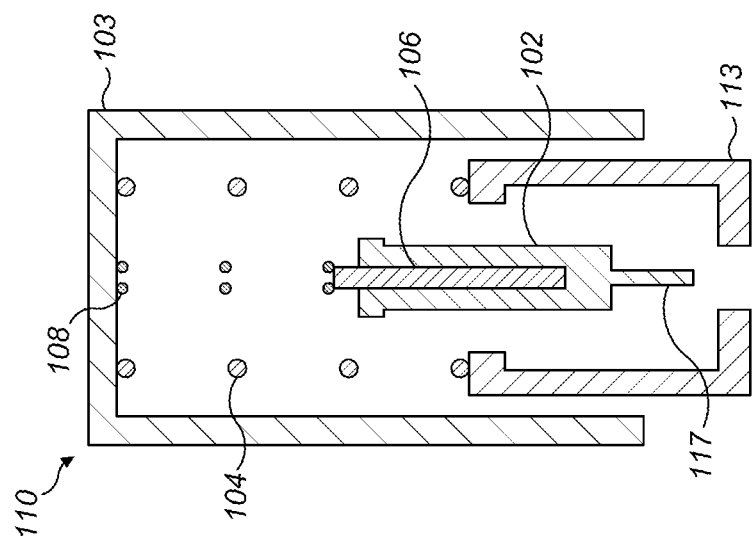
FIG. 2C shows a view of the injector device of FIG. 2B after medicament delivery and removal of the injector device from the injection site.
Figure 2B:
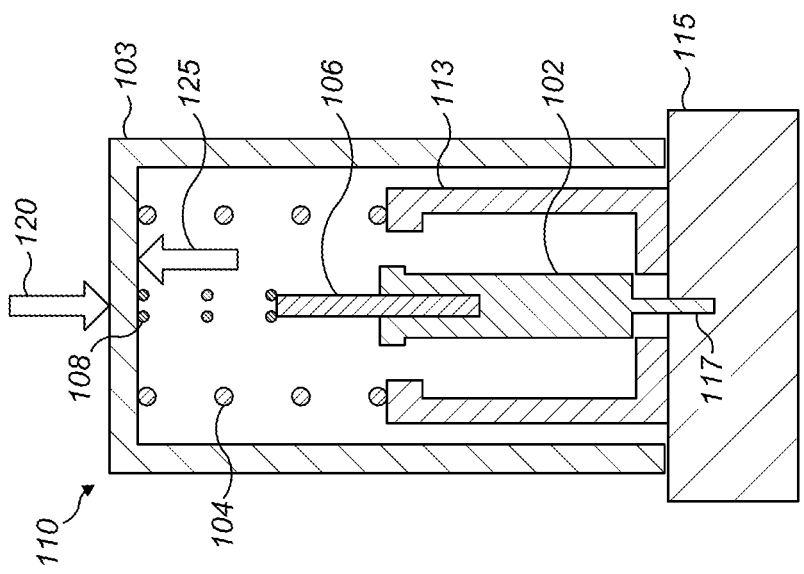
FIG. 2B shows a view of the injector device of FIG. 2A in a holding position, during medicament delivery.
Figure 2A:
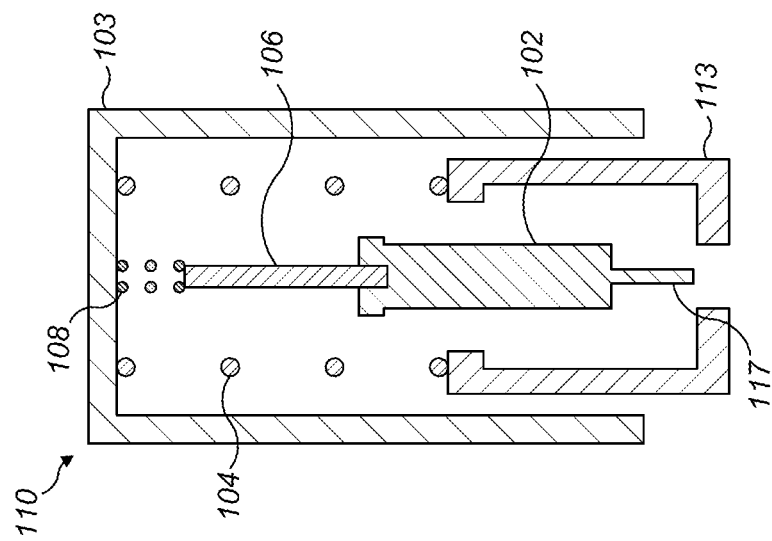
FIG. 2A shows a simplified view of an injector device prior to use.

FIGS. 2A to 2C show a simplified view of a device 110 having a body 103 containing a pre-filled syringe 102 and a needle cover 113. A needle 117 is in fluid communication with the pre-filled syringe 102. The needle cover 113 is axially movable to cover and uncover the needle 117. The needle cover 113 is biased by a spring 104 to extend over the needle 117.

FIG. 2A shows the device 110 before use, in which the needle cover 113 is exposed out of the end of the device body 103 and covers the needle 117. A force can be applied by a user against a spring force 125 to move the needle cover 113 from the position shown in FIG. 2A towards a holding position shown in FIG. 2B, and a holding force 120 can be applied to maintain the needle cover 113 in the holding position.

Typically, the user presses the needle cover 113 against an injection site 115 to push the needle cover 113 at least partially into the device body 103. The exposed needle 117 is pushed into the injection site 115. In the holding position shown in FIG. 2B, medicament is automatically dispensed from the needle 117 via an automated mechanism, for example a plunger 106 axially driven by a drive spring 108. A user typically holds the needle cover 113 in the holding position for a predetermined period of time, to ensure that the correct dose of medicament is dispensed from the device 110, before removing the device 110 from the injection site 115.

The spring force 125 against which the user applies a force to move the needle cover 113 is one component of the "activation force" of the device 110. The activation force refers to the force or force profile that the user exerts on the device 110 to move the needle cover 113 from the position shown in FIG. 2A to the position shown in FIG. 2B. If this force or force profile is not well balanced, it can lead to difficulty in activating the device 110 for some users, or increase the pain or anxiety associated with using the device 110. Furthermore, certain users such as those with dexterity issues may find difficulty in maintaining the device 110 in the holding position during medicament delivery due to the spring force 125 provided by the spring 104.

After the completion of medicament delivery, the user removes the device 110 from the injection site 115. The needle cover 113 is biased by the spring 104 to move axially out of the body 103 and extend over the needle 117. The device 110 is now in a post-use state, as shown in FIG. 2C.

FIGS. 3A to 3D show features of a medicament delivery device 300, which is also referred to herein as an injector device. These Figures show a cross-section of the device 300 during various stages of use of the device 300 during medicament delivery.

The device 300 has a distal end 302 and a proximal end 304 arranged along a longitudinal axis of the device 300. The device 300 has a needle 306 for injecting medicament into a user at an injection site S (such as the user's skin), a needle cover 308 and a body 310 (also known as a housing). The body 310 may be substantially cylindrical and has a substantially constant diameter along the longitudinal axis of the device 300.

The body 310 forms part of the external surface of the device 300 and is configured to be gripped by a user.

The device 300 houses a pre-filled syringe 312 and may comprise a carrier to support the pre-filled syringe 312 within the body 310. The needle 306 is in fluid communication with the pre-filled syringe 312 and extends from the distal end of the pre-filled syringe 312. The needle cover 308 is axially movable relative to the body 310 between an initial, extended position shown in FIG. 3A, in which the needle cover 308 covers the needle 306, and a retracted position, shown in FIGS. 3B & 3C, for dispensing medicament from the device 300. In the retracted position, the needle 306 protrudes from the distal end of the needle cover 308.

Medicament is dispensed from the medicament delivery device 300 via the needle 306 while the needle cover 308 is in the retracted position. An automated mechanism is triggered to start the dispensing of medicament when the needle cover 308 reaches a predetermined axial position within the body 310. The predetermined position may be located just distally of the retracted position. However, in other examples the predetermined position may be located at the retracted position, or just proximally of the retracted position.

The automated mechanism may comprise a plunger 316. The plunger 316 is axially movable relative to the body 310 in a distal direction from a proximal position to a distal position, to dispense medicament from the pre-filled syringe 312. The plunger 316 is automatically released when the needle cover 308 reaches the predetermined axial position. When the plunger 316 is released, it moves within the pre-filled syringe 312 to dispense medicament from the syringe 312 through the needle 306. The plunger 316 may be moved to dispense the medicament by application of a force from a drive spring 318, although other forms of drive mechanism for providing a drive force to the plunger 316 may be used instead, such as an electromechanical motor or a gas cartridge.

The device 300 comprises a needle cover biasing mechanism 314 (which may comprise a spring) is configured to exert a biasing force against the needle cover 308 to bias the needle cover 308 axially, in the distal direction, from the retracted position of the needle cover 308 to the extended position of the needle cover 308. A force can be applied by a user against the biasing force of the needle cover biasing mechanism 314 to move the needle cover 308 from the extended position shown in FIG. 3A towards the retracted position shown in FIG. 3B.

The device 300 comprises a locking mechanism 350 (shown in FIGS. 3B and 3C) configured to be moved by the plunger 316 from an initial configuration to an engaged configuration to prevent a distal movement of the needle cover biasing mechanism 314 relative to the body 310. When the locking mechanism 350 is in its initial configuration, the needle cover biasing mechanism 314 is able to move distally and to transfer a biasing force to the needle cover 308 to bias the needle cover 308 into its extended position. By moving the locking mechanism 350 from its initial configuration to its engaged configuration to prevent a distal movement of the needle cover biasing mechanism 314 relative to the body 310, the locking mechanism 350 in turn prevents the needle cover biasing mechanism 314 from axially moving the needle cover 308 relative to the body 310 in a distal direction under the influence of the biasing force (e.g. provided by the spring). The needle cover biasing mechanism 314 is therefore held in a fixed axial position with respect to the body 310 when the locking mechanism 350 is in its engaged configuration.

In use, the user may remove a cap from the distal end 302 of the medicament delivery device 300. The user presses the needle cover 308 against an injection site S, such as the user's skin 315, to move the needle cover 308 axially relative to the body 310 and to uncover the needle 306. The needle 306 is pushed into the injection site S. The automated mechanism is released, and medicament is automatically dispensed from the device 300 via the needle 306. The user holds the needle cover 308 in the activated position while the medicament is dispensed.

Figure 3B:
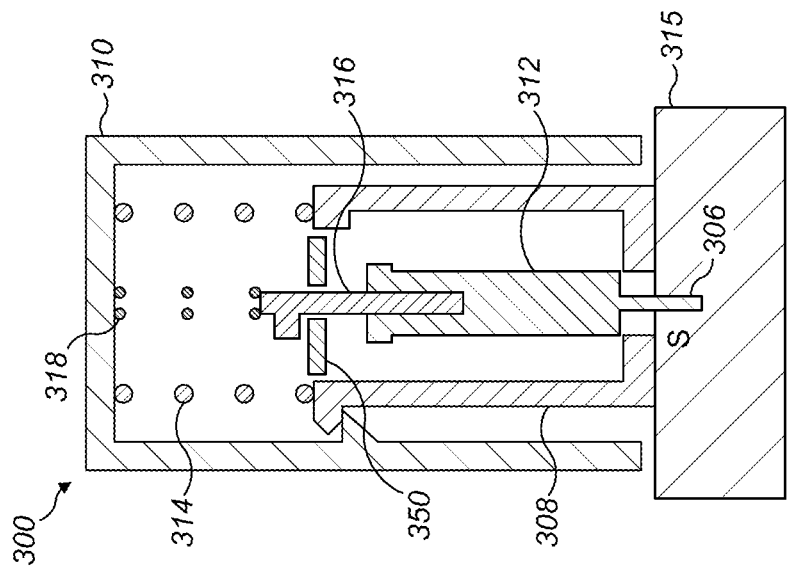
FIG. 3B shows the medicament delivery device of FIG. 3A at the start of medicament delivery.
Figure 3A:
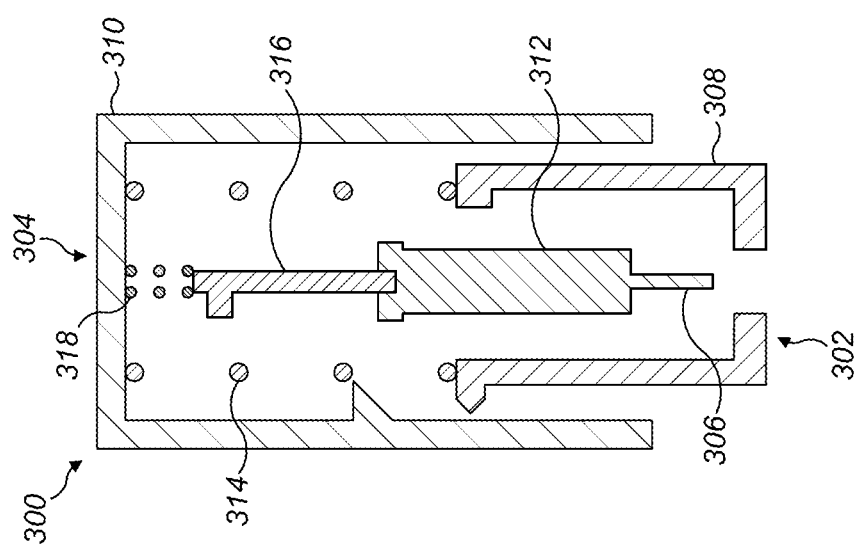
FIG. 3A shows a medicament delivery device in an initial state.

FIG. 3A shows the device 300 in a pre-use state, which may also be called an initial state or initial position. The needle cover 308 covers the needle 306 in this position. The needle cover biasing mechanism 314 (which may comprise a shuttle member coupled to a spring) applies a distal biasing force to the needle cover 308, which biases the needle cover 308 into its extended position to cover the needle 306. The locking mechanism 350 is in a first configuration in which the locking mechanism 350 does not prevent the needle cover biasing mechanism 314 from axially moving the needle cover 308 in a distal direction from its retracted position to its extended position. The needle cover 308 is therefore free to move axially between its extended position and retracted position. The needle cover biasing mechanism 314 may prevent movement of the locking mechanism 350 from its initial configuration until the needle cover 308 has been moved to its retracted position.

FIG. 3B shows the device 300 in an activated state. To move the device 300 from the pre-use state of FIG. 3A to the activated state of FIG. 3B, the user applies a distal force via the body 310 while the needle cover 308 is placed against the user's skin 315 at the injection site S, thereby causing the needle cover 308 to move proximally into the device 300 from its extended position to its retracted position and cause the needle 306 to protrude from the distal end 302 of the needle cover 308.

When the device 300 is in the activated state as shown in FIG. 3B, the needle cover 308 is fully displaced into the device 300 and is in its retracted position. The needle 306 protrudes from the end of the needle cover 308 to its maximum extent. The medicament dispensing mechanism of the device 300 is triggered. In this example, triggering of the dispensing mechanism comprises the drive spring 318 being released such that the drive spring 318 expands from a compressed state to an extended state, applying a distal driving force to the plunger 316 of the pre-filled syringe 312. The distal driving force causes the plunger 316 to move distally and in turn cause medicament to be expelled from the pre-filled syringe 312 via the needle 306.

Distal movement of the plunger 316 from its proximal position causes the locking mechanism 350 to be moved from its initial configuration to its engaged configuration. That is, the plunger 316 engages with the locking mechanism 350 as it moves axially from its proximal position towards its distal position to move the locking mechanism 350 from its initial configuration to its engaged configuration. When the locking member 350 is in its engaged configuration, a distal movement of the needle cover biasing mechanism 314 is prevented. This means that the needle cover biasing mechanism 314 is prevented from axially moving the needle cover 308 relative to the body 310 in a distal direction under the influence of the biasing force (e.g. provided by the spring). The needle cover biasing mechanism 314 is therefore held in a fixed axial position with respect to the body 310 when the locking mechanism 350 is in its engaged configuration and the biasing force provided by the needle cover biasing mechanism 314 (e.g. by the spring of the needle cover biasing mechanism 314) is not transferred to the needle cover 308. The user therefore does not have to overcome the biasing force to hold the device 300 steady at the injection site S during medicament delivery.

Figure 3D:
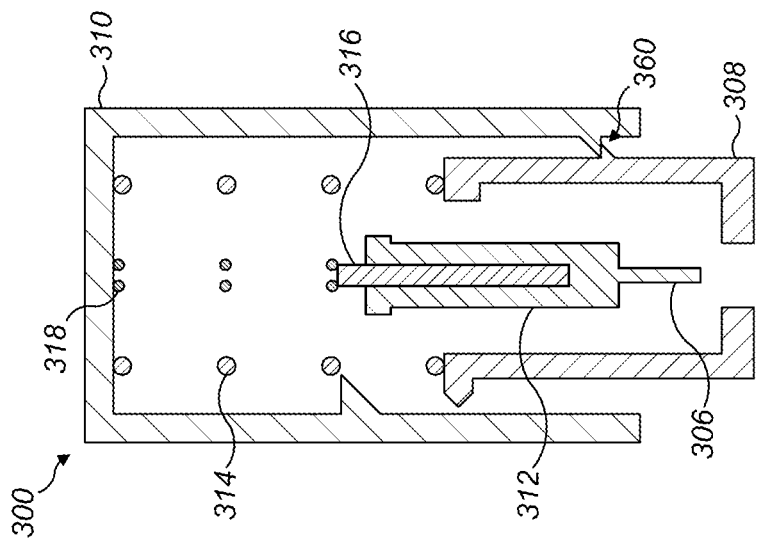
FIG. 3D shows the medicament delivery device of FIG. 3C after medicament delivery and removal of the injector device from the injection site.
Figure 3C:
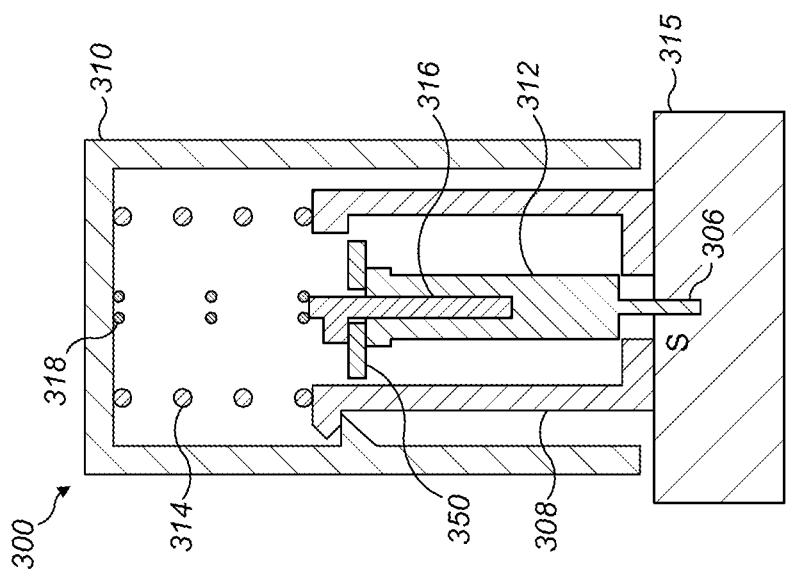
FIG. 3C shows the medicament delivery device of FIG. 3B part-way through medicament delivery.

FIG. 3C shows the device 300 after medicament delivery is almost complete. The plunger 316 has been axially translated in a distal direction from its proximal position towards its distal position due to a driving force exerted on the plunger 316 by the drive spring 318, causing medicament to be expelled in the process. The locking element 350 may have been held in its engaged configuration by the plunger 316 while the plunger 316 moves between its proximal position and distal position, to prevent a distal movement of the needle cover biasing mechanism 314 during delivery of the medicament and therefore prevent the biasing force of the needle cover biasing mechanism 314 from being transferred to the needle cover 308.

Once the plunger 316 reaches its distal position corresponding to completion of the medicament delivery, the locking mechanism 350 may be configured to automatically be moved from its engaged position back to its initial position, in which it is disengaged with the needle cover biasing mechanism 314. The needle cover biasing mechanism 314 may therefore again be free to move axially, to transfer the biasing force to the needle cover 308.

FIG. 3D shows the device 300 after the completion of medicament delivery and after the device 300 has been removed from the user's skin 315. Since the needle cover biasing mechanism 314 is no longer being held by the locking mechanism 350, the needle cover biasing mechanism 314 once again applies a biasing force to the needle cover 308 to bias the needle cover 308 distally. As such, once the needle cover 308 is removed from the user's skin 315, the needle cover 308 translates distally due to the biasing force until it again extends over the needle 306. The needle cover 308 may have returned to its initial, extended position with respect to the body 310.

In some examples, as the needle cover 308 returns to its extended position, a needle cover latch 360 may be activated to inhibit subsequent proximal movement of the needle cover 308 relative to the body 310, and therefore prevent exposure of the needle 306 outside the needle cover 308. The needle cover latch 360 may comprise a first engaging feature disposed on the needle cover 308 and a second engaging feature disposed on a different part of the device 300 such as the body 310.

FIGS. 4A to 4E shows features of a medicament delivery device 400, which is also referred to herein as an injector device. These Figures each show a cross section of the device 400 during various stages of use of the device 400 during medicament delivery.

The device 400 has a distal end 402 and a proximal end 404 arranged along a longitudinal axis Y of the device 400. The device 400 has a needle 406 for injecting medicament into a user at an injection site (such as the user's skin), a needle cover 408 and a body 410 (also known as a housing). The body 410 may be substantially cylindrical and has a substantially constant diameter along the longitudinal axis Y of the device 400. The body 410 forms part of the external surface of the device 400 and is configured to be gripped by a user.

The device 400 houses a pre-filled syringe 412 and a carrier 422 for supporting the pre-filled syringe 412 within the body 410. The needle 406 is in fluid communication with the pre-filled syringe 412 and extends from the distal end of the pre-filled syringe 412. The needle cover 408 is axially movable relative to the body 410 between an initial, extended position shown in FIG. 4A, in which the needle cover 408 covers the needle 406, and a retracted position, shown in FIGS. 4B to 4D, for dispensing medicament from the device 400. In the retracted position, the needle 406 protrudes from the distal end of the needle cover 408.

Medicament is dispensed from the medicament delivery device 400 via the needle 406 while the needle cover 408 is in the retracted position. An automated mechanism is triggered to start the dispensing of medicament when the needle cover 408 reaches a predetermined axial position within the body 410. The predetermined position may be located just distally of the retracted position. However, in other examples the predetermined position may be located at the retracted position, or just proximally of the retracted position.

The automated mechanism may comprise a plunger 416. The plunger 416 is axially movable relative to the body 410 in a distal direction from a proximal position (e.g. shown in FIG. 4A) to a distal position (e.g. shown in FIG. 4D), to dispense medicament from the pre-filled syringe 412. The plunger 416 is automatically released when the needle cover 408 reaches the predetermined axial position. When the plunger 416 is released, it moves distally within the pre-filled syringe 412 to dispense medicament from the syringe 412 through the needle 406. The plunger 416 may be moved to dispense the medicament by application of a force from a drive spring 418, although other forms of drive mechanism for providing a drive force to the plunger 416 may be used instead, such as an electromechanical motor or a gas cartridge. The plunger 416 may exert a force on a bung or piston 420 to expel the medicament from the pre-filled syringe 412.

The device 400 comprises a needle cover biasing mechanism 480 configured to exert a biasing force against the needle cover 408 in a distal direction to bias the needle cover 408 axially, in the distal direction, from the retracted position of the needle cover 408 to the extended position of the needle cover 408. A force can be applied by a user against the biasing force of the needle cover biasing mechanism 480 to move the needle cover 408 from the extended position shown in FIG. 4A towards the retracted position shown in FIG. 4B.

Figure 4A:
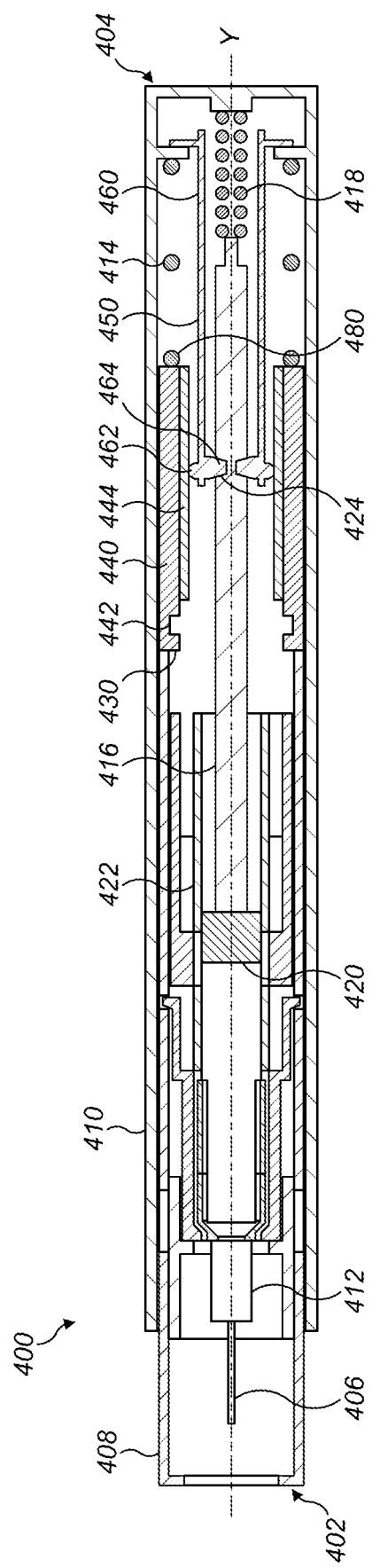
FIG. 4A shows a medicament delivery device in an initial state prior to use.
Figure 4B:
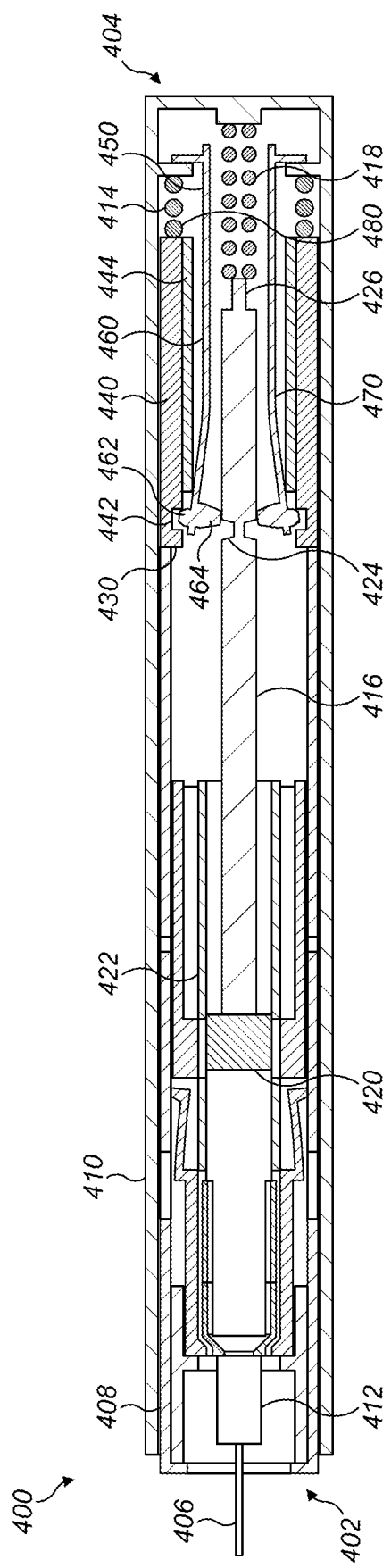
FIG. 4B shows the medicament delivery device of FIG. 4A in an activated state.

The device 400 comprises a locking mechanism 450 configured to be moved by the plunger 416 from an initial configuration shown in FIG. 4A to an engaged configuration shown in FIG. 4B, to prevent a distal movement of the needle cover biasing mechanism 480 relative to the body 410. When the locking mechanism 450 is in its initial configuration, the needle cover biasing mechanism 480 is able to move distally and to transfer a biasing force to the needle cover 408 to bias the needle cover 408 into its extended position. By moving the locking mechanism 450 from its initial configuration to its engaged configuration to prevent a distal movement of the needle cover biasing mechanism 480 relative to the body 410, the locking mechanism 450 in turn prevents the needle cover biasing mechanism 480 from axially moving the needle cover 408 relative to the body 410 in a distal direction under the influence of the biasing force (e.g. provided by a spring 414 of the needle cover biasing mechanism 480). The needle cover biasing mechanism 480 is therefore held in a fixed axial position with respect to the body 410 when the locking mechanism 450 is in its engaged configuration.

In use, the user may remove a cap from the distal end 402 of the medicament delivery device 400. The user presses the needle cover 408 against an injection site S, such as the user's skin 415, to move the needle cover 408 axially relative to the body 410 and to uncover the needle 406. The needle 406 is pushed into the injection site S. The automated mechanism is released, and medicament is automatically dispensed from the device 400 via the needle 406. The user holds the needle cover 408 in the activated position while the medicament is dispensed.

FIG. 4A shows the device 400 in a pre-use state, which may also be called an initial state or initial position. The needle cover 408 covers the needle 406 in this position. The needle cover biasing mechanism 480 comprises a shuttle member 430 and the spring 414 (or another form of biasing member). The spring 414 is configured to exert a distal biasing force on the shuttle member 430 which biases the shuttle member 430 axially, towards the distal end 402 of the medicament delivery device 400. The shuttle member 430 is in turn configured to transfer the biasing force to the needle cover 408 to bias the needle cover 408 distally from its retracted position to its extended position to cover the needle 406. The shuttle member 430 is axially movable within the body 410 of the device 400 to transfer the biasing force to the needle cover 408. In some examples the shuttle member 430 and the needle cover 408 may be joined together (e.g. at a proximal end of the needle cover 408 and a distal end of the shuttle member 430) such that they are integrally formed to form a combined unit that can move in unison. However, in other examples the shuttle member 430 may abut the needle cover 408 without being permanently joined to the needle cover 408. FIG. 4A shows the shuttle member 430 taking the form of a collar arranged along the longitudinal axis Y of the device 400, between the needle cover 408 and the spring 414, the collar comprising an outer collar 440 and an inner collar 444 coupled to, and arranged concentrically within, the outer collar 440. However, it should be envisaged that the shuttle member 430 may in other examples take a form other than a collar. A first slot 442 is dispose on an inner surface of the shuttle member 430, in this example on an inner surface of the outer collar 440. The first slot 442 may be a recess or aperture formed at the inner surface of the shuttle member 430.

FIG. 4A shows the locking mechanism 450 comprising a resilient member 460 which takes the form of a flexible arm which extends axially (or longitudinally) and which has a first protrusion 462 and a second protrusion 464 on the free end of the flexible arm. The first protrusion 462 extends radially from the flexible arm away from the plunger 416 and towards an inner surface of the shuttle member 430 (in particular an inner surface of the inner collar 444) to engage with inner surface of the shuttle member 430. The second protrusion 464 extends radially from the flexible arm in an opposite direction to the first protrusion 462, towards the plunger 416 to engage with a second slot 424 in an outer surface of the plunger 416. The second slot 424 may be a recess or aperture formed on the plunger 416.

The locking mechanism 450 is shown in FIG. 4A in its initial configuration in which the locking mechanism 450 does not prevent the needle cover biasing mechanism 480 from axially moving the needle cover 408 in a distal direction from its retracted position to its extended position. The needle cover 408 is therefore free to move axially between its extended position and retracted position. The needle cover 408 is in its extended position, which means the shuttle member 430 is in a corresponding distal position. The resilient member 460 (and more particularly, the second protrusion 464) is configured to engage the second slot 424 when the locking mechanism 450 is in its initial configuration, to inhibit distal movement of the plunger from its proximal position by the drive spring 418. While the second protrusion 464 is engaged in the second slot 424, the needle cover 408 is in its extended position and the shuttle member 430 is in its distal position, the first protrusion 462 is held against an inner surface of the shuttle member 430 (e.g. an inner surface of the inner collar 444) to prevent deflection of the resilient member 460 away from the plunger 416 and therefore can ensure the second protrusion 464 remains engaged with the second slot 424. The needle cover biasing mechanism 480 (and more particularly the shuttle member 430) therefore prevents movement of the locking mechanism 450 from its initial configuration until the needle cover 408 has been moved to its retracted position.

FIG. 4B shows the device 400 in an activated state. To move the device 400 from the pre-use state of FIG. 4A to the activated state of FIG. 4B, the user applies a distal force via the body 410 while the needle cover 408 is placed against the user's skin 415 at the injection site, thereby causing the needle cover 408 to move proximally into the device 400 from its extended position to its retracted position and cause the needle 406 to protrude from the distal end of the needle cover 408, as shown in FIG. 4B. Proximal movement of the needle cover 408 also causes proximal movement of the shuttle member 430 to a proximal position of the shuttle member 430.

When the device 400 is in the activated state as shown in FIG. 4B, the needle cover 408 is fully displaced into the device 400 and is in its retracted position, with the shuttle member 430 in its proximal position. The needle 406 protrudes from the end of the needle cover 408 to its maximum extent. The medicament dispensing mechanism of the device 400 is triggered in response to the shuttle member 430 reaching its proximal position. More specifically, as the shuttle member 430 is moved proximally by the needle cover 408, the first protrusion 462 is held against, and slides along, the inner surface of the shuttle member 430 (e.g. an inner surface of the inner collar 444), thus maintaining engagement between the second protrusion 464 and the second slot 424 to inhibit distal movement of the plunger 416 from its proximal position. Once the shuttle member 430 reaches its distal position, the first protrusion 462 becomes aligned with the first slot 442 in the inner surface of the shuttle member 430 such that the first protrusion 462 is no longer held against the inner surface of the shuttle member 430 and is free to enter and engage the first slot 442. Since the first protrusion 462 is no longer held against the inner surface of the shuttle member 430, a slight distal movement of the plunger 416 by the driving force of the drive spring 418 causes the resilient member 460 to be deflected and to disengage the second slot 424. In particular, the flexible arm of the resilient member 460 bends outwards as the second protrusion 464 exits the second slot 424. Distal movement of the plunger 416 from its proximal position therefore causes the locking mechanism 450 to be moved from its initial configuration to its engaged configuration. A distal-facing edge of the second slot 424 and/or a proximal-facing edge of the second protrusion 464 may be beveled to assist with causing the resilient member 460 to be deflected away from the plunger 416 as the plunger 416 begins to move.

Once the second protrusion 464 has disengaged from the second slot 424, the drive spring 418 is fully released such that the drive spring 418 expands from a compressed state to an extended state, applying a distal driving force to the plunger 416 of the pre-filled syringe 412. The distal driving force causes the plunger 416 to continue moving distally and in turn cause medicament to be expelled from the pre-filled syringe 412 via the needle 406.

Figure 4C:
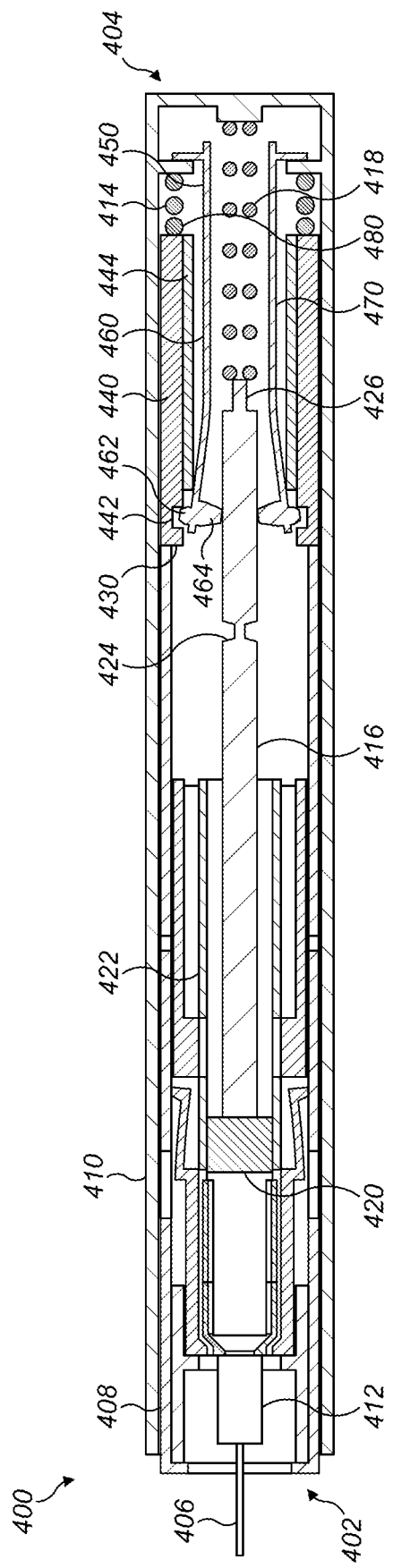
FIG. 4C shows the medicament delivery device of FIG. 4B during medicament delivery.

FIG. 4C shows the plunger 416 in an intermediate position between its proximal position and its distal position. As the plunger 416 moves distally, the second protrusion 464 engages an outer surface of the plunger 416, causing the resilient member 460 to be deflected such that the first protrusion 462 enters and engages the first slot 442 in the shuttle member 430. The locking mechanism 450 has therefore been moved from its initial configuration to its engaged configuration by the plunger 416.

When the locking member 450 is in its engaged configuration with the first protrusion 462 engaged in the first slot 442, a distal movement of the needle cover biasing mechanism 480 is prevented. This means that the needle cover biasing mechanism 480 is prevented from axially moving the needle cover 408 relative to the body 410 in a distal direction under the influence of the biasing force (e.g. provided by the spring 414). The needle cover biasing mechanism 480 is therefore held in a fixed axial position with respect to the body 410 when the locking mechanism 450 is in its engaged configuration and the biasing force provided by the needle cover biasing mechanism 480 (e.g. by the spring 414 of the needle cover biasing mechanism 480) is not transferred to the needle cover 408. The user therefore does not have to overcome the biasing force to hold the device 400 steady at the injection site during medicament delivery.

The resilient member 460 is held in the first slot 442 by the outer surface of the plunger 416 while the plunger 416 moves between its proximal position and distal position, to prevent a distal movement of the needle cover biasing mechanism 480.

Figure 4D:
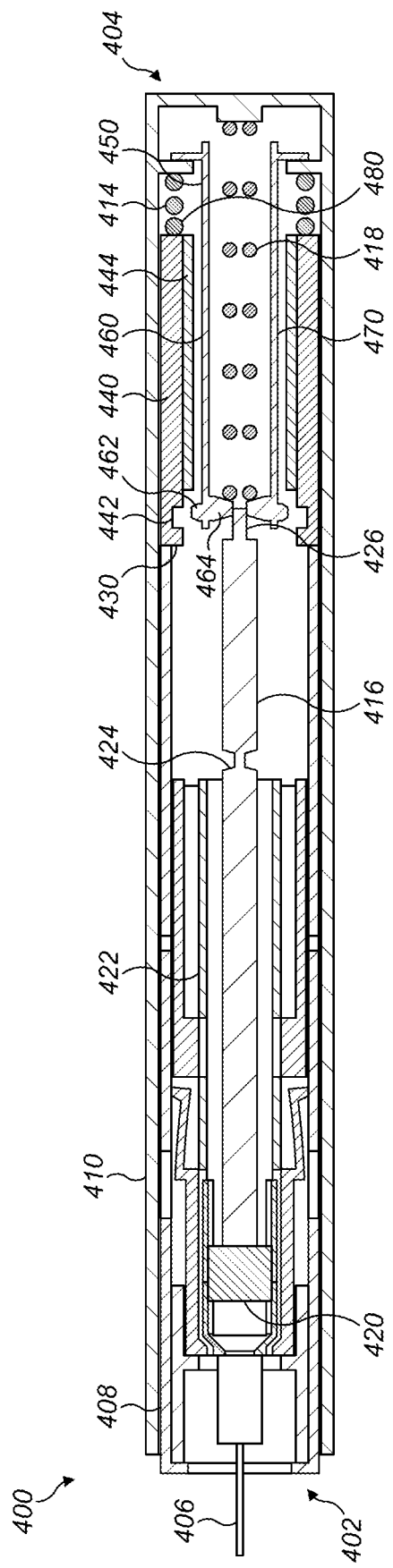
FIG. 4D shows the medicament delivery device of FIG. 4C after medicament delivery is complete.

As shown in FIG. 4D, once the plunger 416 reaches its distal position corresponding to completion of the medicament delivery, the locking mechanism 450 may be configured to automatically be moved from its engaged configuration back to its initial configuration, in which it is disengaged with the needle cover biasing mechanism 480. More specifically, the resilient member 460 is configured to disengage from the first slot 442 responsive to the plunger 416 reaching its distal position. This may occur due to the second protrusion 464 reaching the proximal end of the plunger 416 or aligning with a third slot 426 disposed at the outer surface of the plunger 460 when the plunger 416 reaches its distal position. When the second protrusion 464 reaches the proximal end of the plunger 416 or aligns with the third slot 426, the second protrusion 464 is no longer held against the outer surface of the plunger 416 and so the resilient member 460 (and more specifically the flexible arm) is caused to bend inwards, back towards its initial configuration, due to the resiliency of the resilient member 460. As the resilient member 460 returns to its initial configuration, the first protrusion 462 disengages the first slot 442, therefore the locking mechanism 450 no longer prevents a distal movement of the needle cover biasing mechanism 480. As such the needle cover biasing mechanism 480 may therefore again be free to move axially, to transfer a biasing force from the spring 414 to the needle cover 408.

Figure 4E:
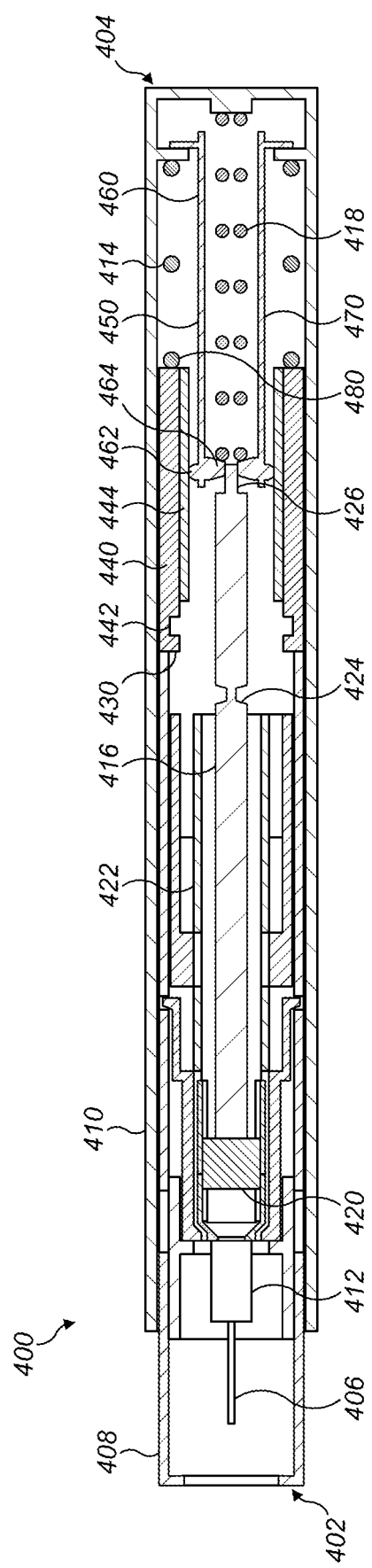
FIG. 4E shows the medicament delivery device of FIG. 4D after removal of the medicament delivery device from the injection site.

FIG. 4E shows the device 400 after the completion of medicament delivery and after the device 400 has been removed from the injection site. Since the needle cover biasing mechanism 480 is no longer being held by the needle cover holding mechanism 450 (i.e. the first protrusion 462 is no longer engaged with the first slot 442, the needle cover biasing mechanism 480 is once again able to exert a biasing force to the needle cover 408 to bias the needle cover 408 distally. As such, once the needle cover 408 is removed from the injection site, the needle cover 408 translates distally due to the biasing force until it again extends over the needle 406. The needle cover 408 may therefore have returned to its initial, extended position with respect to the body 410.

In some examples, as the needle cover 408 returns to its extended position, a needle cover latch may be activated to inhibit subsequent proximal movement of the needle cover 408 relative to the body 410, and therefore prevent exposure of the needle 406 outside the needle cover 408. The needle cover latch may comprise a first engaging feature disposed on the needle cover 408 and a second engaging feature disposed on a different part of the device 400 such as the body 410.

FIGS. 4A to 4E show two resilient members 460 disposed opposite each other in the body 410, on opposite sides of the plunger 416, each with a respective first protrusion 462 configured to engage a respective first slot 442 and a respective second protrusion 464 configured to engage a respective second slot 424. Such a configuration may allow for the locking mechanism 450 to more securely hold the needle cover biasing member 480 and/or the plunger 416, which may improve the safety of the device 400 and/or reduce the likelihood of an accidental triggering of the medicament dispensing process. However, it should be understood that in other examples only a single resilient member 460 with a single first protrusion 462, single second protrusion 464, single first slot 442 and single second slot 424 may be present in the device 400, while in other examples three or more resilient members 460 may be present, with a corresponding number of first protrusions 462, second protrusions 464, first slots 442 and second slots 424 present in the device 400.

Figure 5:
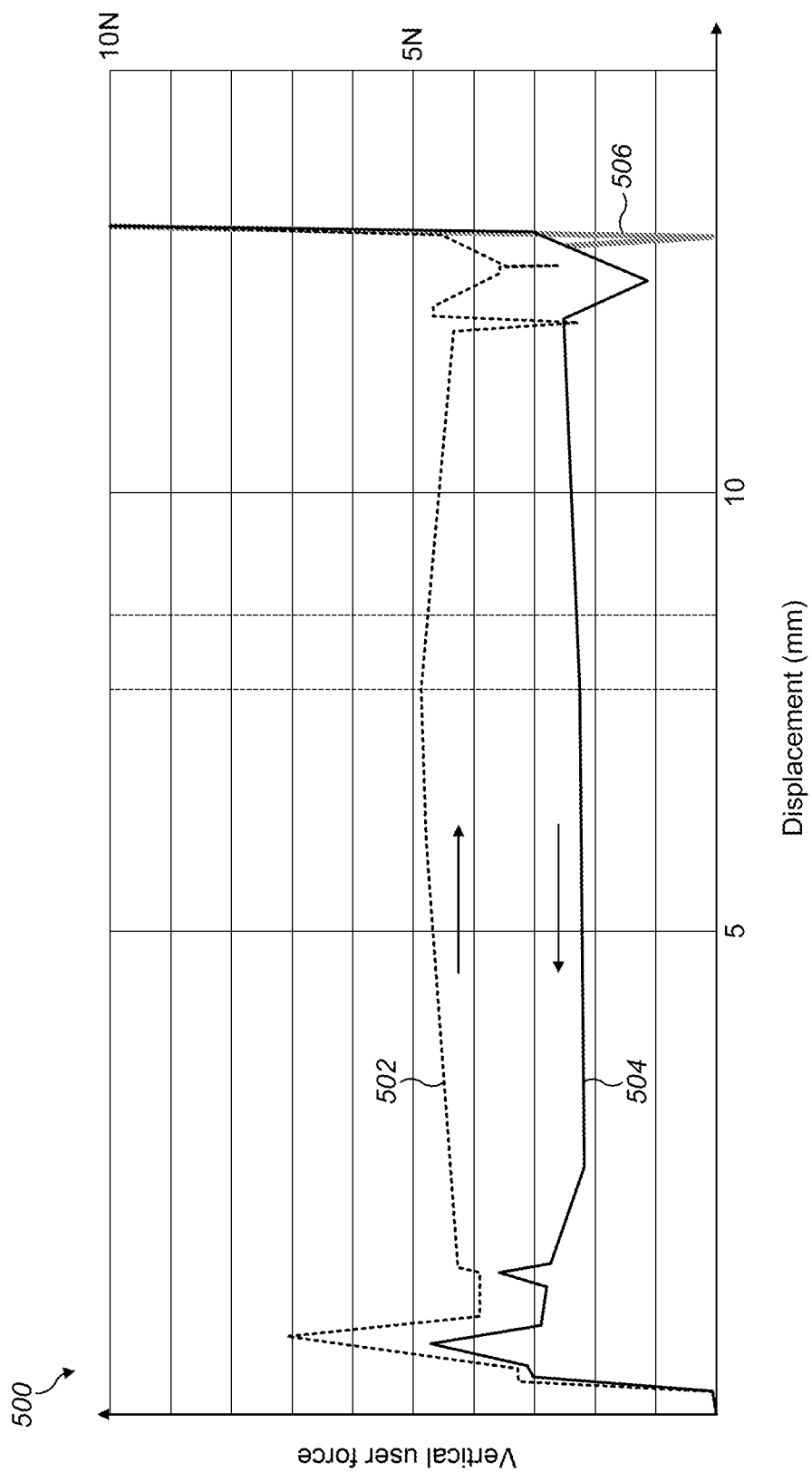
FIG. 5 is a force profile graph illustrating the force profile of a first device and a medicament delivery device.

Referring to FIG. 5, a force profile graph 500 is shown illustrating the force profile of a first device 110 and a medicament delivery device, such as the medicament delivery device 300 or 400 described herein. The horizontal axis is the displacement of the needle cover of the device in millimeters (mm) and the vertical axis is the user applied force in Newtons (N).

The first trace 502 shows the force profile of the activation force of the first device 110 and the medicament delivery device, such as the medicament delivery device 300 or 400, when the user is pushing the first device 110 or medicament delivery device 300 or 400 onto an injection site. The force profile when initially pushing the first device 110 and medicament delivery device 300 or 400 onto an injection site may be substantially similar for the first device 110 and medicament delivery device 300 or 400.

The second trace 504 shows the force profile of the first device 110 when the user is holding and then removing the first device 110 from the injection site during and after completion of medicament delivery. It can be seen that when the needle cover of the first device 110 is at a maximum displacement (i.e. when the user is maximally pressing the first device 110 against the injection site and holding the first device 110 in place as the medicament is being delivered), the vertical user force the user applies to the first device 110 is non-zero to overcome the biasing force of the spring 104.

In contrast, the third trace 506 represents the force profile of the medicament delivery device 300 or 400 near maximum displacement of the needle cover 308 or 408, as the user is holding the device 300 or 400 steady during medicament delivery. The plunger 316 or 416 has moved the locking mechanism 350 or 450 from an initial configuration to an engaged configuration in which it prevents distal movement of the needle cover biasing mechanism 314 or 480, therefore the needle cover biasing mechanism 314 or 480 can no longer transfer a biasing force to the needle cover 308 or 408. As such, the third trace 506 shows that the vertical user force applied to the medicament delivery device 300 or 400 is zero, since the user no longer overcomes a biasing force provided to the needle cover to hold the device 300 or 400 steady during medicament delivery. Once medicament delivery is complete and the plunger 316 or 416 has moved to its distal position, the locking mechanism 350 or 450 moves back from its engaged configuration to its initial configuration, disengaging the needle cover biasing mechanism 314 or 480. Distal movement of the needle cover biasing mechanism 314 or 480 is no longer prevented, and therefore the needle cover biasing mechanism 314 or 480 can once again transfer a biasing force to the needle cover 308 or 408. Therefore, once medicament delivery is complete and the user removes the medicament delivery device 300 or 400 from the injection site, the medicament delivery device 300 or 400 may follow a force profile similar to that of the second trace 504 for the first device 110.

While embodiments have been generally disclosed herein in which a locking mechanism 350 or 450 is used to engage and disengage a needle cover biasing mechanism 314 or 480, in alternative embodiments the locking mechanism 350 or 450 may be used to directly engage and disengage the needle cover 308 or 408 itself.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (SIRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders.

Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F (ab) and F (ab') 2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the devices and method disclosed herein include, for example, Fab fragments, F (ab') 2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014 (E). As described in ISO 11608-1: 2014 (E), needle-based injection systems may be broadly distinguished into multi-dose container systems and single-dose (with partial or full evacuation) container systems. The container may be a replaceable container or an integrated non-replaceable container.

As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

10—drug delivery device
11—housing
11a—window
12—cap
13—needle sleeve
14—reservoir
15—medicament
17—needle
20—distal region
21—proximal region
22—button
23—bung or piston
102—pre-filled syringe
103—device body
104—spring
106—plunger
108—drive spring
110—device
113—needle cover
115—injection site
117—needle
120—holding force
125—spring force
300—medicament delivery device
302—distal end
304—proximal end
306—needle
308—needle cover
310—body
312—pre-filled syringe
314—needle cover biasing mechanism
315—skin
316—plunger
318—drive spring
350—locking mechanism
360—needle cover latch
400—medicament delivery device
402—distal end
404—proximal end
406—needle
408—needle cover
410—body
412—pre-filled syringe
414—spring
416—plunger
418—drive spring
420—bung or piston
422—carrier
424—second slot
426—third slot
430—shuttle member
440—outer collar
442—first slot
444—inner collar
450—locking mechanism
460—resilient member
462—first protrusion
464—second protrusion
480—needle cover biasing mechanism
500—force profile graph
502—first trace
504—second trace
506—third trace

The invention claimed is:

1. A medicament delivery device comprising:
a needle for injecting medicament, the needle disposed at a distal end of the medicament delivery device;
a body configured to receive a syringe;
a needle cover axially movable relative to the body between an extended position, in which a distal end of the needle cover is distal to a distal end of the needle, and a retracted position, in which the distal end of the needle is distal to the distal end of the needle cover;
a plunger axially movable relative to the body from a proximal position to a distal position to dispense a medicament from the medicament delivery device;
a needle cover biasing mechanism configured to bias the needle cover distally from the retracted position to the extended position; and
a locking mechanism configured to be moved by the plunger from an initial configuration to an engaged configuration to limit a distal movement of the needle cover biasing mechanism relative to the body.

2. The medicament delivery device of claim 1, wherein distal movement of the plunger from the proximal position causes the locking mechanism to be moved from the initial configuration to the engaged configuration.

3. The medicament delivery device of claim 1, wherein the needle cover biasing mechanism is configured to limit movement of the locking mechanism from the initial configuration until the needle cover has moved to the retracted position.

4. The medicament delivery device of claim 1, wherein the needle cover biasing mechanism comprises a shuttle member and a spring, wherein the spring is configured to exert a biasing force on the shuttle member which biases the shuttle member axially towards the distal end of the medicament delivery device, and the shuttle member is configured to transfer the biasing force to the needle cover to bias the needle cover distally from the retracted position to the extended position.

5. The medicament delivery device of claim 1, wherein the needle cover biasing mechanism comprises one or more first slots and wherein the locking mechanism comprises one or more resilient members, wherein the one or more resilient members are each configured to be received by a respective one of the one or more first slots after movement of the locking mechanism from the initial configuration to the engaged configuration by the plunger such that when the one or more resilient members are in the one or more first slots, distal movement of the needle cover biasing mechanism relative to the body is limited.

6. The medicament delivery device of claim 5, wherein the one or more resilient members each comprise a flexible arm and a first protrusion disposed on an end of the flexible arm, wherein each first protrusion of the one or more resilient members is configured to be received by a respective one of the one or more first slots after movement of the locking mechanism from the initial configuration to the engaged configuration by the plunger such that when each first protrusion is in the respective one or more first slots, distal movement of the needle cover biasing mechanism is limited.

7. The medicament delivery device of claim 5, wherein the one or more resilient members are each held in a respective one of the one or more first slots by an outer surface of the plunger while the plunger moves between the proximal position and the distal position.

8. The medicament delivery device of claim 5, wherein the one or more resilient members are configured to disengage from the respective one of the one or more first slots when the plunger is in the distal position.

9. The medicament delivery device of claim 5, wherein the one or more first slots are recesses or apertures.

10. The medicament delivery device of claim 5, wherein the plunger comprises one or more second slots, and wherein the one or more resilient members are each configured to engage a respective one of the one or more second slots when the locking mechanism is in the initial configuration such that when the one or more resilient members are engaged to the one or more second slots, distal movement of the plunger from the proximal position relative to the body is limited.

11. The medicament delivery device of claim 10, wherein the one or more second slots comprise recesses or apertures.

12. The medicament delivery device of claim 10, wherein at least one of a distal-facing edge of each of the one or more second slots or a proximal-facing edge of each of one or more second protrusions is beveled.

13. The medicament delivery device of claim 10, wherein the one or more resilient members are each configured to disengage the respective one of the one or more second slots responsive to the needle cover being moved to the retracted position.

14. The medicament delivery device of claim 1, further comprising a drive spring configured to exert a force on the plunger which biases the plunger axially towards the distal end of the medicament delivery device.

15. The medicament delivery device of claim 1, further comprising the syringe containing the medicament.

16. A medicament delivery device comprising:
a body configured to contain a syringe;
a needle cover axially movable relative to the body between an extended position, in which the needle cover covers a needle coupled to the syringe, and a retracted position, in which the needle protrudes from a distal end of the needle cover;
a plunger configured to dispense a medicament from the medicament delivery device;
a needle cover biasing mechanism configured to bias the needle cover from the retracted position to the extended position; and
a locking mechanism configured to be actuated by a first movement of the plunger relative to the body such that when the locking mechanism is actuated, the locking mechanism limits the needle cover biasing mechanism from biasing the needle cover to the extended position.

17. The medicament delivery device of claim 16, wherein the needle cover biasing mechanism comprises a shuttle member and a biasing member, the biasing member being configured to exert a force on the shuttle member to bias the needle cover from the retracted position to the extended position.

18. The medicament delivery device of claim 17, wherein the shuttle member and the needle cover define a monolithic structure.

19. The medicament delivery device of claim 17, wherein the biasing member comprises a spring.

20. The medicament delivery device of claim 16, wherein the locking mechanism comprises a resilient member configured to be deflected by the first movement of the plunger.

21. The medicament delivery device of claim 20, wherein the resilient member is configured to be deflected by the first movement of the plunger to engage a first slot of the needle cover biasing mechanism to limit the needle cover biasing mechanism from biasing the needle cover to the extended position.

22. The medicament delivery device of claim 21, wherein the resilient member comprises a flexible arm and a first protrusion disposed on an end of the flexible arm, wherein the first protrusion is configured to enter the first slot to limit the needle cover biasing mechanism from biasing the needle cover to the extended position.

23. The medicament delivery device of claim 21, wherein the resilient member is configured to be held in engagement with the first slot by an outer surface of the plunger during a second movement of the plunger, the second movement subsequent to the first movement.

24. The medicament delivery device of claim 23, wherein the second movement occurs during medicament delivery.

25. The medicament delivery device of claim 23, wherein the resilient member is configured to disengage from the first slot during a third movement of the plunger to cause the needle cover biasing mechanism to bias the needle cover to the extended position, the third movement subsequent to the second movement.

26. The medicament delivery device of claim 25, wherein the third movement corresponds to a completion of medicament delivery.

27. The medicament delivery device of claim 21, wherein the plunger comprises a second slot, and wherein the resilient member is configured to engage the second slot while the needle cover is in the extended position to limit the first movement of the plunger.

28. The medicament delivery device of claim 27, wherein the resilient member is configured to disengage the second slot responsive to the needle cover being moved to the retracted position such that when the resilient member is disengaged from the second slot, the first movement of the plunger is allowed.

29. The medicament delivery device of claim 16, further comprising a drive spring configured to move the plunger and the syringe containing the medicament.

30. A medicament delivery device comprising:
   a needle for injecting medicament, the needle disposed at a distal end of the medicament delivery device;
   a body configured to receive a syringe;
   a needle cover axially movable relative to the body between an extended position, in which the needle cover covers the needle, and a retracted position, in which the needle protrudes from a distal end of the needle cover;
   a plunger axially movable relative to the body from a proximal position to a distal position to dispense a medicament from the medicament delivery device;
   a collar;
   a spring configured to bias the collar towards the needle cover to distally bias the needle cover from the retracted position to the extended position; and
   a resilient member configured such that when the plunger moves from the proximal position towards the distal position, the resilient member changes from a first configuration in which the spring distally biases the needle cover towards the extended position and a second configuration in which the spring does not distally bias the needle cover towards the extended position.

* * * * *